United States Patent
Lee et al.

(10) Patent No.: US 10,959,850 B2
(45) Date of Patent: Mar. 30, 2021

(54) IMPLANT HAVING POROUS LAYER AND MOLDING METHOD THEREOF

(71) Applicant: Corentec Co., LTD, Cheonan-si (KR)

(72) Inventors: Goon-Hee Lee, Seoul (KR); Oui-Sik Yoo, Seoul (KR); Young-Woong Jang, Seoul (KR)

(73) Assignee: Corentec Co., LTD., Cheonan-si (KR)

( * ) Notice: Subject to any disclaimer, the term of this patent is extended or adjusted under 35 U.S.C. 154(b) by 465 days.

(21) Appl. No.: 15/605,465

(22) Filed: May 25, 2017

(65) Prior Publication Data

US 2017/0348107 A1    Dec. 7, 2017

Related U.S. Application Data

(60) Provisional application No. 62/343,940, filed on Jun. 1, 2016.

(51) Int. Cl.
*A61F 2/30* (2006.01)
*A61F 2/40* (2006.01)
(Continued)

(52) U.S. Cl.
CPC ...... *A61F 2/30767* (2013.01); *A61F 2/30771* (2013.01); *A61F 2/30907* (2013.01); *A61F 2/3094* (2013.01); *A61F 2/32* (2013.01); *A61F 2/38* (2013.01); *A61F 2/40* (2013.01); *A61F 2/4202* (2013.01); *A61F 2002/3092* (2013.01); *A61F 2002/3093* (2013.01);
(Continued)

(58) Field of Classification Search
CPC .......... A61F 2/389; A61F 2/3859; A61F 2/28; A61F 2002/3092; A61F 2002/3093; A61F 2/30767; A61F 2002/30985; A61F 2310/00029; A61F 2/30734; A61F 2/461; A61F 2002/4205; A61F 2/30; A61F 2/34; A61F 2/32; A61F 2/36

See application file for complete search history.

(56) References Cited

U.S. PATENT DOCUMENTS 4,479,271 A * 10/1984 Bolesky .............. A61F 2/30907
                                                      623/20.17
5,080,674 A *  1/1992 Jacobs ................ A61F 2/30734
                                                      623/20.17

(Continued)

*Primary Examiner* — William H Matthews
(74) *Attorney, Agent, or Firm* — Workman Nydegger

(57) ABSTRACT

An implant having a porous layer and a molding method thereof includes: a substrate having a bone contact surface being in part in direct contact with a bone of a patient; a porous layer having a void inside; a connecting layer disposed between the bone contact surface and the porous layer to attach the bone contact surface to the porous layer; and a rib detachably coupled to the porous layer, wherein the connecting layer includes at least one constituent component identical to one of constituent components in the bone contact surface to be integrated into the porous layer and the bone contact surface, thereby firmly attaching the porous layer to the bone contact surface. Accordingly, bonding of dissimilar metals is facilitated by inducing the attachment of the bone contact surface of the implant to the porous layer having a void inside, formed by dissimilar metals, through the connecting layer including at least one constituent component identical to one of constituent components of the bone contact surface.

9 Claims, 9 Drawing Sheets

(51) Int. Cl.
*A61F 2/38* (2006.01)
*A61F 2/32* (2006.01)
*A61F 2/42* (2006.01)

(52) U.S. Cl.
CPC ........... *A61F 2002/30593* (2013.01); *A61F 2002/30909* (2013.01); *A61F 2002/30971* (2013.01); *A61F 2002/30985* (2013.01); *A61F 2310/00023* (2013.01); *A61F 2310/00029* (2013.01); *A61F 2310/00041* (2013.01); *A61F 2310/00059* (2013.01); *A61F 2310/00101* (2013.01)

(56) References Cited

U.S. PATENT DOCUMENTS

| | | | | |
|---|---|---|---|---|
| 6,049,054 | A * | 4/2000 | Panchison | A61F 2/30907 219/121.64 |
| 2007/0142914 | A1* | 6/2007 | Jones | A61F 2/30907 623/14.13 |

* cited by examiner

IMPLANT HAVING POROUS LAYER AND MOLDING METHOD THEREOF

CROSS-REFERENCE TO RELATED APPLICATIONS

This application claims the benefit of U.S. Provisional Application No. 62/343,940, filed Jun. 1, 2016, which is incorporated herein by specific reference.

FIELD OF THE INVENTION

The present invention relates to an implant having a porous layer and a molding method thereof and, more specifically, to an implant having a porous layer and a molding method thereof, comprising: a substrate having a bone contact surface being a part in direct contact with a bone of a patient; a porous layer having a void inside; a connecting layer disposed between the bone contact surface and the porous layer to attach the bone contact surface to the porous layer; and a rib detachably coupled to the porous layer, wherein the connecting layer includes at least one constituent component identical to one of constituent components in the bone contact surface to be integrated into the porous layer and the bone contact surface, thereby firmly attaching the porous layer to the bone contact surface. Accordingly, bonding of dissimilar metals is facilitated by inducing the attachment of the bone contact surface of the implant to the porous layer having a void inside, formed by dissimilar metals, through the connecting layer including at least one constituent component identical to one of constituent components of the bone contact surface.

BACKGROUND OF THE INVENTION

In case a bone in a joint area is destroyed or joint damage causes the joint to malfunction due to arthritis or bone tumor, the joint is resected and an artificial joint is replaced in the resected joint area through a surgical procedure. Such artificial joint replacement surgery is targeted, such as at shoulder, hip, knee, and ankle joints. A stem, a peg, a spike, and the like may be formed in an implant to attach the artificial joint to a bone of a patient, and improved attachment may be achieved by applying bone cement to a bone contact surface of the implant, which contacts the bone of the patient.

Such artificial joint replacement surgery may cause side effects, such as an osteolysis phenomenon where the bone attached to a prosthesis is dissolved, infection at the surgical site, dislocation of the prosthesis, nerve paralysis, and pain, the cause of which can be found in improper attachment of the implant placed inside the body of the patient to the bone of the patient.

Accordingly, inducing natural bone growth of the patient may be of more importance than a securing means, such as a stem and bone cement, in artificial joint replacement surgery. Consequently, there is a tendency in the relevant art to adopt a porous structure that can promote bone growth of the patient on the bone contact surface of the implant.

FIG. 1 shows a prior art representing a knee bone implanted with an artificial knee joint implant, disclosed in Korea Patent No. 10-1704954 (2017 Feb. 9). Referring to FIG. 1, the artificial knee joint implant 90 mainly comprises a femoral element 91 attached to a distal end of a femur F, a tibial element 93 attached to a proximal end of a tibia T, and a bearing element 95 disposed between the femoral element 91 and the tibial element 93.

Setting aside the bearing element 95, the femoral element 91 and the tibial element 93 retains the bone contact surface which directly contacts with the bone of the patient. In order to maintain a state where the femoral element 91 and the tibial element 93 are secured stably to the bone of the patient for a long period of time, not only should the bone contact surface be strongly attached to the bone of the patient at the time of surgery, but also the implant should conglutinate with the bone of the patient by stimulating natural bone growth of the patient.

This does not apply only to the case of the artificial knee joint implant 90 but also to bone contact surfaces of all implants used in artificial joint surgery.

As described above, in order to advance bone growth of the patient, it is common to form a porous layer having numerous voids in the bone contact surface of the implant, which can quickly promote conglutination of the implant with the bone overall as the bone of the patient grows and develops in between minute voids of the porous layer.

The porous layer may be formed by biomaterials which are biocompatible and nontoxic, such as titanium, titanium alloy, cobalt-chromium, magnesium, and the like, to suppress side effects on body after artificial joint surgery. In manufacturing the implant having such porous layer, after a prosthesis having a smooth surface (hereinafter, "substrate") is manufactured, the porous layer is separately coated to the bone contact surface of the substrate.

However, the process of coating the porous layer to the substrate presents difficulty since bonding the substrate to the porous layer, which may be made of different materials, is required. This is because bonding the same materials is simple, whereas bonding the dissimilar materials is not easy. Therefore, the relevant industry is looking for a technique which may more easily and firmly attach the porous layer that can prompt bone growth and development of the patient to the bone contact surface of the substrate.

SUMMARY OF THE INVENTION

Technical Problem

The present invention has been made in an effort to solve the problems.

An object of the present invention is to provide an implant having a porous layer comprising a substrate having a bone contact surface being a part in direct contact with a bone of a patient; a porous layer having a void inside; and a connecting layer disposed between the bone contact surface and the porous layer to couple the bone contact surface and the porous layer such that bonding of dissimilar metals is facilitated by inducing the attachment of the bone contact surface of the implant to the porous layer having a void inside, formed by dissimilar metals, through the connecting layer including at least one constituent component identical to one of constituent components of the bone contact surface.

Another object of the present invention is to provide an implant having a porous layer, wherein the connecting layer integrates with the porous layer and the bone contact surface to firmly attach the porous layer to the bone contact surface, which allows firm bonding through the connecting layer although the porous layer and the bone contact surface of the substrate are formed by dissimilar metals.

Yet another object of the present invention is to provide an implant having a porous layer, wherein the connecting layer includes at least one constituent component identical to one of constituent components in the bone contact surface, which facilitates bonding of dissimilar metals by inducing the attachment of the bone contact surface of the implant to the porous layer having a void inside, formed by dissimilar metals, through the connecting layer including at least one constituent component identical to one of constituent components of the bone contact surface.

Yet another object of the present invention is to provide an implant having a porous layer, wherein the connecting layer is formed by dissolving a metal thin film to allow firm attachment of the porous layer and the bone contact surface as the connecting layer is disposed between the porous layer and the bone contact surface before the porous layer and the bone contact surface are joined and then formed by dissolved metal thin film under application of heat and pressure.

Yet another object of the present invention is to provide an implant having a porous layer, wherein the thin film is formed as a monolayer or polylayers which allows proper joining strength to be selected by adjusting thickness of the connecting layer produced in accordance with a state of the porous layer and the bone contact surface.

Yet another object of the present invention is to provide an implant having a porous layer, wherein the connecting layer is formed by temporarily joining the metal thin film between the bone contact surface and the porous layer through a temporary fixing means, which allows the metal thin film to contact with and temporarily fix the bone contact surface and the porous layer at a predetermined, correct position until the metal thin film is dissolved to form the connecting layer.

Yet another object of the present invention is to provide an implant having a porous layer, wherein a rib detachably coupled to the porous layer is formed such that the rib coupled to one side of the porous layer supports the porous layer until complete joining of the bone contact surface and the porous layer, thereby preventing twisting of the porous layer.

Yet another object of the present invention is to provide an implant having a porous layer being any one of a shoulder joint, a hip joint, a knee joint, and an ankle joint, which can be applied to various implants implanted into a human bone, such that the porous layer promoting autogenous bone graft substrate is easily attached to the bone contact surface of the substrate.

Yet another object of the present invention is to provide an implant having a porous layer, wherein the bone contact surface is formed by at least one of titanium, titanium alloy, cobalt-chromium, magnesium, and cobalt-chromium-molybdenum alloy to have biocompatibility without rejection when the implant is implanted into a body of the patient.

Yet another object of the present invention is to provide a method for molding an implant having a porous layer, comprising a substrate providing step which provides the substrate having the bone contact surface being a part in direct contact with the bone of the patient; a porous layer forming step which forms a porous layer having a void inside; and a connecting layer forming step which forms a connecting layer disposed between the bone contact surface and the porous layer and attaching the bone contact surface to the porous layer, which facilitates bonding of dissimilar metals by inducing the attachment of the bone contact surface of the implant to the porous layer having a void inside, formed by dissimilar metals, through the connecting layer including at least one constituent component identical to one of constituent components of the bone contact surface.

Yet another object of the present invention is to provide a method for molding an implant having a porous layer, wherein the connecting layer forming step comprises: a metal thin film providing step which provides a metal thin film which forms the connecting layer; a temporarily joining step which temporarily joins the metal thin film between the bone contact surface and the porous layer through a temporary fixing means; and a hot isostatic pressing step which attaches the bone contact surface to the porous layer by applying heat and pressure, which facilitates bonding of dissimilar metals by inducing the attachment of the bone contact surface of the implant to the porous layer having a void inside, formed by dissimilar metals, through the connecting layer including at least one constituent component identical to one of constituent components of the bone contact surface.

Yet another object of the present invention is to provide a method for molding an implant having a porous layer, wherein the connecting layer forming step further comprises a rib providing step which provides a rib that supports the porous layer by being detachably coupled to the porous layer before the hot isostatic pressing step; and a rib removing step which removes the rib after the hot isostatic pressing step, which prevents twisting of the porous layer by the rib coupled to one side of the porous layer and capable of uniformly supporting the porous layer until complete joining of the bone contact surface and the porous layer.

Yet another object of the present invention is to provide a method for molding an implant having a porous layer, wherein the substrate providing step comprises a casting step which manufactures an orthopedic prosthesis; a heat-treating step which changes mechanical characteristics by heat-treating the cast orthopedic prosthesis; a machining step which processes the orthopedic prosthesis passing the heat-treating step; a blasting step which removes surface impurities of the orthopedic prosthesis finished with the machining; and a polishing step which polishes surfaces of the orthopedic prosthesis, which provides a biocompatible orthopedic prosthesis having the bone contact surface.

Yet another object of the present invention is to provide a method for molding an implant having a porous layer, wherein the porous layer forming step comprises a powder providing step which provides powder; a 3D printing step which forms a three-dimensional structure of the porous layer by using the powder provided through the powder providing step; and a post-treating step being a post-treatment process of the porous layer produced by the 3D printing step such that the porous layer having a three-dimensional shape and multiple minute voids is easily manufactured as a complementary shape to the shape of the implant bone contact surface.

Technical Solution

In order to achieve the above object, the present invention is realized by embodiments having the following features.

According to one embodiment of the present invention, an implant having a porous layer according to the present invention comprises: a substrate having a bone contact surface being a part in direct contact with a bone of a patient; a porous layer having a void inside; and a connecting layer disposed between the bone contact surface and the porous layer to attach the bone contact surface to the porous layer.

According to another embodiment of the present invention, in the implant having the porous layer, the connecting layer integrates with the porous layer and the bone contact surface to firmly attach the porous layer to the bone contact surface.

According to still another embodiment of the present invention, in the implant having the porous layer, the connecting layer includes at least one constituent component identical to one of constituent components in the bone contact surface.

According to still another embodiment of the present invention, in the implant having the porous layer, the connecting layer is formed by dissolving a metal thin film.

According to still another embodiment of the present invention, in the implant having the porous layer, the metal thin film is formed as a monolayer or polylayers.

According to still another embodiment of the present invention, in the implant having the porous layer, the connecting layer is formed by temporarily joining the metal thin film between the bone contact surface and the porous layer through a temporary fixing means.

According to still another embodiment of the present invention, the implant having the porous layer further comprises a rib detachably coupled to the porous layer.

According to still another embodiment of the present invention, the implant is any one of a shoulder joint, a hip joint, a knee joint, and an ankle joint.

According to still another embodiment of the present invention, in the implant having the porous layer, the bone contact surface is formed by at least one of titanium, titanium alloy, cobalt-chromium, magnesium, and cobalt-chromium-molybdenum alloy.

According to still another embodiment of the present invention, a method for molding an implant having a porous layer comprises: a substrate providing step which provides a substrate having a bone contact surface being a part in direct contact with a bone of a patient; a porous layer forming step which forms a porous layer having a void inside; and a connecting layer forming step which forms a connecting layer disposed between the bone contact surface and the porous layer and attaching the bone contact surface to the porous layer.

According to still another embodiment of the present invention, in the method for molding an implant having a porous layer, the connecting layer integrates with the porous layer and the bone contact surface to firmly attach the porous layer to the bone contact surface.

According to still another embodiment of the present invention, in the method for molding an implant having a porous layer, the connecting layer includes at least one constituent component identical to one of constituent components in the bone contact surface.

According to still another embodiment of the present invention, in the method for molding an implant having a porous layer, the connecting layer forming step comprises: a metal thin film providing step which provides a metal thin film which forms the connecting layer; a temporarily joining step which temporarily joins the metal thin film between the bone contact surface and the porous layer through a temporary fixing means; and a hot isostatic pressing step which attaches the bone contact surface to the porous layer by applying heat and pressure.

According to still another embodiment of the present invention, in the method for molding an implant having a porous layer, the metal thin film is formed as a monolayer or polylayers.

According to still another embodiment of the present invention, in the method for molding an implant having a porous layer, the connecting layer forming step further comprises: a rib providing step which provides a rib that supports the porous layer by being detachably coupled to the porous layer before the hot isostatic pressing step; and a rib removing step which removes the rib after the hot isostatic pressing step.

According to still another embodiment of the present invention, in the method for molding an implant having a porous layer, the substrate providing step comprises: a casting step which manufactures an orthopedic prosthesis; a heat-treating step which changes mechanical characteristics by heat-treating the cast orthopedic prosthesis; a machining step which processes the orthopedic prosthesis passing the heat-treating step; a blasting step which removes surface impurities of the orthopedic prosthesis finished with the machining; and a polishing step which polishes surfaces of the orthopedic prosthesis.

According to still another embodiment of the present invention, in the method for molding an implant having a porous layer, the porous layer forming step comprises: a powder providing step which provides powder; a 3D printing step which forms a three-dimensional structure of the porous layer by using the powder provided through the powder providing step; and a post-treating step being a post-treatment process of the porous layer produced by the 3D printing step.

Advantageous Effects

According to the above-described embodiments and the following features, combinations, and relations of use that will be described later, the present invention can obtain the following effects.

According to the present invention, an implant having a porous layer is provided, comprising a substrate having a bone contact surface being a part in direct contact with a bone of a patient; a porous layer having a void inside, and a connecting layer disposed between the bone contact surface and the porous layer to couple the bone contact surface and the porous layer such that bonding of dissimilar metals is facilitated by inducing the attachment of the bone contact surface of the implant to the porous layer having a void inside, formed by dissimilar metals, through the connecting layer including at least one constituent component identical to one of constituent components of the bone contact surface.

According to the present invention, an implant having a porous layer is provided, wherein the connecting layer integrates with the porous layer and the bone contact surface to firmly attach the porous layer to the bone contact surface, which allows firm bonding through the connecting layer although the porous layer and the bone contact surface of the substrate are formed by dissimilar metals.

According to the present invention, an implant having a porous layer is provided, wherein the connecting layer includes at least one constituent component identical to one of constituent components in the bone contact surface, which facilitates bonding of dissimilar metals by inducing the attachment of the bone contact surface of the implant to the porous layer having a void inside, formed by dissimilar metals, through the connecting layer including at least one constituent component identical to one of constituent components of the bone contact surface.

According to the present invention, an implant having a porous layer is provided, wherein the connecting layer is formed by dissolving a metal thin film to allow firm attachment of the porous layer and the bone contact surface as the connecting layer is disposed between the porous layer and the bone contact surface before the porous layer and the bone contact surface are joined and then formed by dissolving metal thin film under application of heat and pressure.

According to the present invention, an implant having a porous layer is provided, wherein the thin film is formed as a monolayer or polylayers which allows proper joining strength to be selected by adjusting thickness of the connecting layer produced in accordance with a state of the porous layer and the bone contact surface.

According to the present invention, an implant having a porous layer is provided, wherein the connecting layer is formed by temporarily joining the metal thin film between the bone contact surface and the porous layer through a temporary fixing means, which allows the metal thin film to contact with and temporarily fix the bone contact surface and the porous layer at a predetermined, correct position until the metal thin film is dissolved to form the connecting layer.

According to the present invention, an implant having a porous layer is provided, wherein a rib detachably coupled to the porous layer is formed such that the rib coupled to one side of the porous layer supports the porous layer until complete joining of the bone contact surface and the porous layer, which prevents twisting of the porous layer, thereby preventing twisting of the porous layer.

According to the present invention, an implant having a porous layer is provided, the implant being any one of a shoulder joint, a hip joint, a knee joint, and an ankle joint, which can be applied to various implants implanted into a human bone, such that the porous layer promoting autogenous bone graft to the bone contact surface of the substrate is easily attached to the bone contact surface of the substrate.

According to the present invention, an implant having a porous layer is provided, wherein the bone contact surface is formed by at least one of titanium, titanium alloy, cobalt-chromium, magnesium, and cobalt-chromium-molybdenum alloy to have biocompatibility without rejection hen the implant is implanted into a body of the patient.

According to the present invention, a method for molding an implant having a porous layer is provided, comprising a substrate providing step which provides the substrate having the bone contact surface being a part in direct contact with the bone of the patient; a porous layer forming step which forms a porous layer having a void inside; and a connecting layer forming step which forms a connecting layer disposed between the bone contact surface and the porous layer and attaching the bone contact surface to the porous layer, which facilitates bonding of dissimilar metals by inducing the attachment of the bone contact surface of the implant to the porous layer having a void inside, formed by dissimilar metals, through the connecting layer including at least one constituent component identical to one of constituent components of the bone contact surface.

According to the present invention, a method for molding an implant having a porous layer is provided, wherein the connecting layer forming step comprises: a metal thin film providing step which provides a metal thin film which forms the connecting layer; a temporarily joining step which temporarily joins the metal thin film between the bone contact surface and the porous layer through a temporary fixing means; and a hot isostatic pressing step which attaches the bone contact surface to the porous layer by applying heat and pressure, which facilitates bonding of dissimilar metals by inducing the attachment of the bone contact surface of the implant to the porous layer having a void inside, formed by dissimilar metals, through the connecting layer including at least one constituent component identical to one of constituent components of the bone contact surface.

According to the present invention, a method for molding an implant having a porous layer is provided, wherein the connecting layer forming step further comprises: a rib providing step which provides a rib that supports the porous layer by being detachably coupled to the porous layer before the hot isostatic pressing step; and a rib removing step which removes the rib after the hot isostatic pressing step which prevents twisting of the porous layer by the rib coupled to one side of the porous layer and capable of uniformly supporting the porous layer until complete joining of the bone contact surface and the porous layer.

According to the present invention, a method for molding an implant having a porous layer is provided, wherein the substrate providing step comprises a casting step which manufactures an orthopedic prosthesis; a heat-treating step which changes mechanical characteristics by heat-treating the cast orthopedic prosthesis; a machining step which processes the orthopedic prosthesis passing the heat-treating step; a blasting step which removes surface impurities of the orthopedic prosthesis finished with the machining; and a polishing step which polishes surfaces of the orthopedic prosthesis, which provides a biocompatible orthopedic prosthesis having the bone contact surface.

According to the present invention, a method for molding an implant having a porous layer is provided, wherein the porous layer forming step comprises: a powder providing step which provides powder; a 3D printing step which forms a three-dimensional structure of the porous layer by using the powder provided through the powder providing step; and a post-treating step being a post-treatment process of the porous layer produced by the 3D printing step such that the porous layer having a three-dimensional shape and multiple minute voids is easily manufactured as a complementary shape to the shape of the implant bone contact surface.

DETAILED DESCRIPTION OF THE INVENTION

Figure 1:
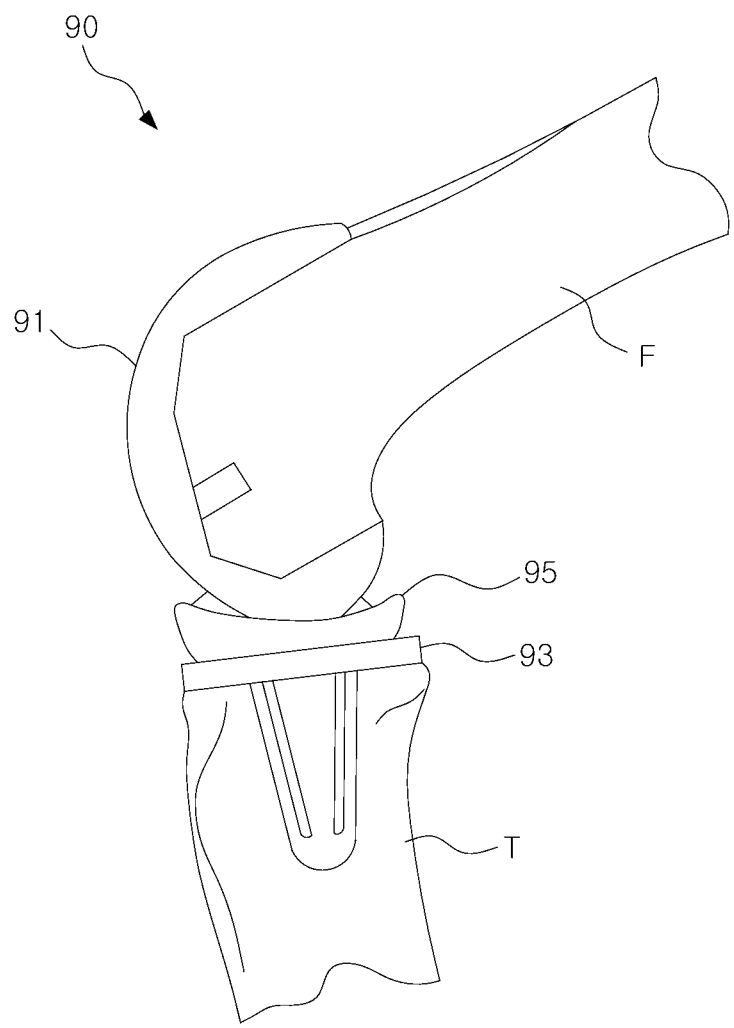
FIG. 1 shows a knee bone implanted with a prior art of an artificial knee joint implant.

Hereinafter, exemplary embodiments of an implant having a porous layer and a molding method thereof according to the present invention will be described with reference to the accompanying drawings. In describing the present invention, well-known functions or constructions will not be described in detail in case they may unnecessarily obscure the understanding of the present invention. Unless not specifically defined, all terminologies in the specification should be interpreted based on the general meanings thereof that a person skilled in the art understands. When the general meanings of the terminologies are incompliant with those used in the specification, the terminologies should be interpreted as being defined herein.

According to one embodiment of the present invention, an implant 1 having a porous layer according to the present invention is a broad concept including artificial joints implanted into a human body. The implant comprises: a substrate 10 having a bone contact surface 101, a porous layer 30, a connecting layer 50, and a rib 70.

The substrate 10 corresponds to an orthopedic prosthesis used in artificial joint replacement surgery on, such as a shoulder joint, a hip joint, a knee joint, and an ankle joint, and the bone contact surface 101 refers to a part which directly contacts with a bone of a patient in the substrate 10. The bone contact surface 101 may be formed by at least one of titanium, titanium alloy, cobalt-chromium, magnesium, and cobalt-chromium-molybdenum alloy.

Figure 2:
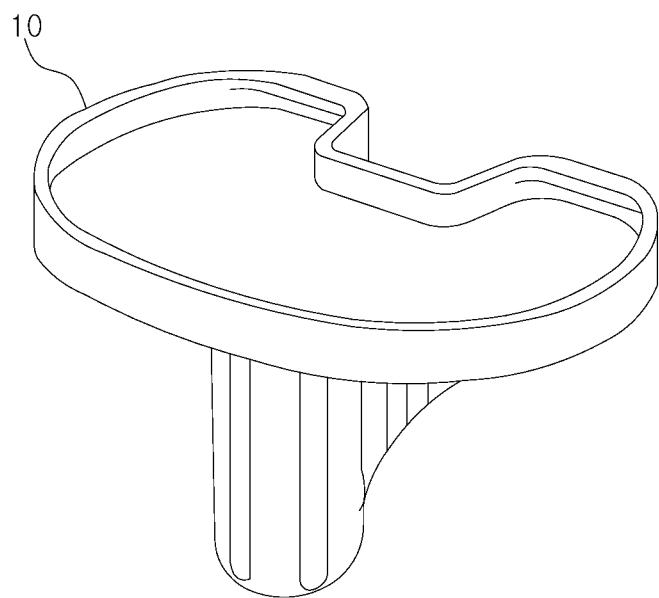
FIG. 2 is a perspective view of a substrate according to the present invention.
Figure 3:
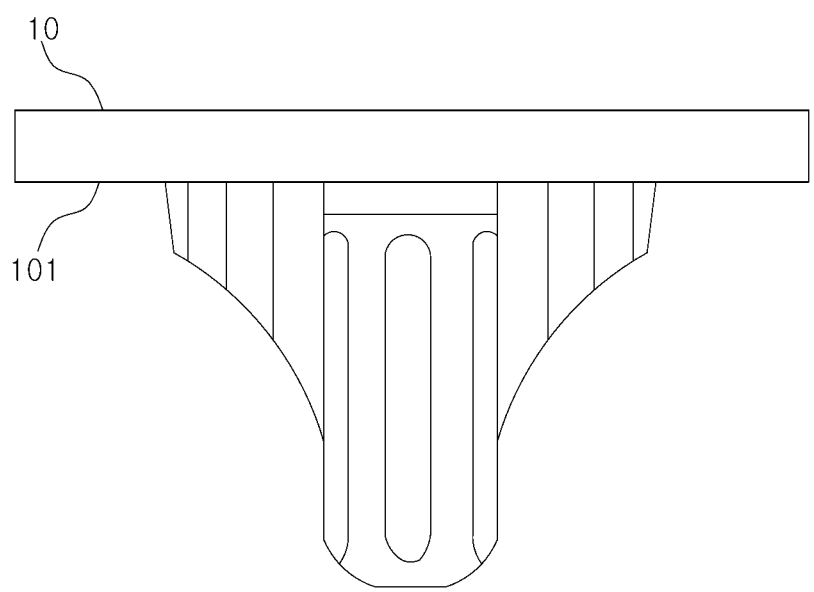
FIG. 3 shows a bone contact surface shown in FIG. 2.

FIG. 2 is a perspective view of the substrate according to the present invention, and FIG. 3 is a view which illustrates the bone contact surface shown in FIG. 2. Referring to FIGS. 2 and 3, represented is a tibial element used in a knee joint replacement surgery among the implants 1. The tibial element is coupled to a proximal end of a tibia of the patient, and the bone contact surface 101 is formed in a lower surface of a base plate in the tibial element as shown in FIG. 3.

Such orthopedic prosthesis may be made of various materials, but it may preferably be formed by cobalt-chromium-molybdenum (CoCrMo) alloy. The orthopedic prosthesis is formed through processes, such as a process of being heat-treated after casting cobalt-chromium-molybdenum (CoCrMo) alloy or the like into a desired shape, machining or grinding, blasting and polishing.

Figure 4:
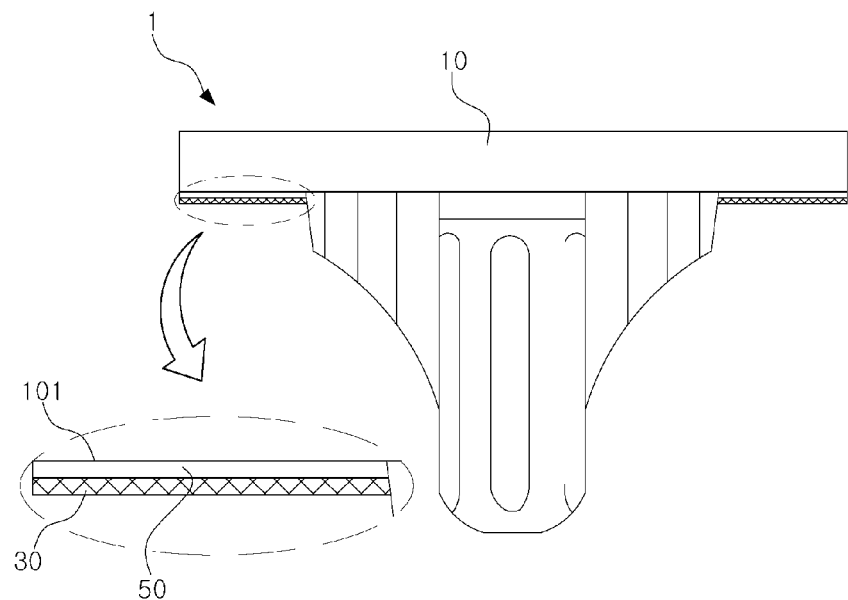
FIG. 4 shows an implant having a porous layer.

FIG. 4 shows the implant having the porous layer. Description will be made in reference to FIG. 4 below.

The porous layer 30 has a three-dimensional structure inside which a void is formed, and there is no particular limit with respect to a shape of the void. However, it is preferable to form the shape and size of the void in such a way as to maximize bone growth efficiency of the patient. The material of the porous layer 30 is not limited to any particular material, but the material may preferably be titanium (Ti).

The porous layer 30 may be formed by a 3D printing method or the like using titanium (Ti) powder and alloy powder based on titanium (Ti) powder. The 3D printing method may preferably adopt a DED (Directed Energy Deposition) method in which powder is supplied in real-time, melted immediately after supply by using a high output laser and stacked or may preferably adopt a PBF (Powder Bed Fusion) method in which a powder layer is spread in a powder bed having a certain area in a powder supply device and piled up by fusing layer by layer after a laser or an electron beam is selectively irradiated. However, the 3D printing method is not limited to above-mentioned methods.

Since the porous layer 30 is an element which is attached to the bone contact surface 101 of the substrate 10, it is preferable for the porous layer 30 to have a shape complementary to the bone contact surface. The porous layer 30 formed through the 3D printing method or the like is finished by going through a post-treatment process, such as cleaning, to enhance biocompatibility.

The connecting layer 50 being positioned between the bone contact surface 101 and the porous layer 30 refers to an element which induces bonding of dissimilar metals. That is, the connecting layer 50 is introduced to attach the porous layer 30 to the bone contact surface 101 of the substrate 10.

Since the substrate 10 and the porous layer 30 are separately formed, components constituting the two elements may not be identical. In this case, elements made of identical materials are easily joined, whereas joining elements made of dissimilar materials may be troublesome. Accordingly, there may be a substantial difficulty in joining the bone contact surface 101 of the substrate 10 to the porous layer 30, when the bone contact surface and the porous layer are made of different materials.

Thus, the connecting layer 50 is configured to include preferably at least one constituent component which is identical to a constituent component of the bone contact surface 101 to facilitate bonding of the substrate 10 and the porous layer 30 made from different materials.

As described above, it becomes difficult to join the bone contact surface 101 and the porous layer 30 being made of different metals since the bone contact surface 101 may preferably be formed by cobalt-chromium-molybdenum (CoCrMo) alloy and the porous layer 30 may preferably be made of titanium (Ti).

Therefore, the connecting layer 50 is formed to have at least one constituent component identical to one of constituent components in the bone contact surface 101 such that the porous layer 30 and the bone contact surface 101 are integrally formed to firmly attach the porous layer 30 to the bone contact surface 101.

The connecting layer 50 is formed by dissolving a metal thin film. That is, the hot isostatic pressing process which is to be later described is performed while the metal thin film is placed in a lower side of the bone contact surface 101 and the porous layer 30 is placed below the metal thin film. Then the metal thin film is melted and produces the connecting layer 50, which induces attachment of the bone contact surface 101 to the porous layer 30.

The material of the metal thin film is not limited to a specific material but may preferably be a molybdenum component, which is one component of the substrate 10 having the bone contact surface 101 of cobalt-chromium-molybdenum (CoCrMo) alloy. In this case, the metal thin film may be formed as a monolayer (mono, 0.01~0.3 μm) or as polylayers (poly, 0.3~10 μm).

In addition, before the metal thin film forms the connecting layer 50 through the hot isostatic pressing process and the bone contact surface 101 and the porous layer 30 are completely joined, the bone contact surface 101 and the porous layer 30 are as if the bone contact surface 101 and the porous layer 30 are in a detached state. Accordingly, before the connecting layer 50 completely joins the bone contact surface 101 and the porous layer 30 through the hot isostatic pressing process, it is necessary to arrange a separate means for temporarily fixing the bone contact surface 101, the metal thin film, and the porous layer 30 stably in predetermined, exact positions. Therefore, the metal thin film may be temporarily joined between the bone contact surface and the porous layer through a temporary fixing means, wherein an adhesive may be used as the temporary fixing means.

Figure 5:
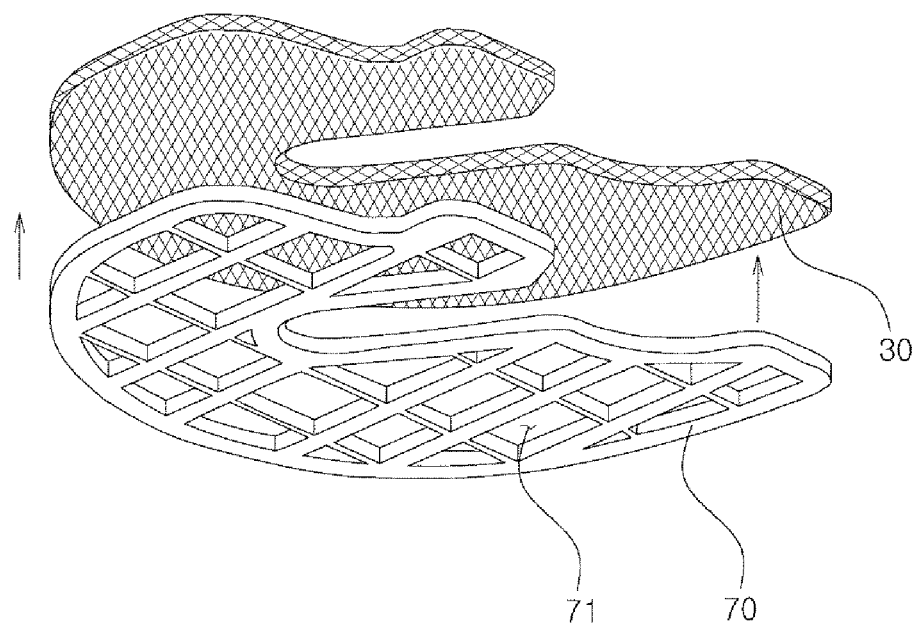
FIG. 5 shows a rib coupled to a connecting layer.

FIG. 5 is a view of a rib joined to the connecting layer. Hereinafter, a description will be provided in reference to FIG. 5.

Although the rib 70 may not be a direct element of the implant 1 having the porous layer, the rib may be used in a manufacturing process of the implant 1 having the porous layer.

Arranged in a lower side of the porous layer 30, the rib 70 supports the porous layer 30 until the porous layer 30 which is to be attached with the bone contact surface 101 is completely joined by the connecting layer 50, and the rib 70 is detachably coupled to the porous layer 30.

It is possible that the porous layer 30 moves by external impact before the porous layer 30 is completely joined with the bone contact surface 101. Also, the porous layer 30 may not be joined uniformly with the bone contact surface 101 and be twisted due to expansion and shrinkage by heat and pressure if the separate means for supporting the porous layer 30 is absent until the metal thin film melts in the bone contact surface 101 and the porous layer by high temperature and high pressure.

Therefore, the rib 70 allows the porous layer 30 to join uniformly with the bone contact surface 101 by supporting the porous layer 30 until the hot isostatic pressing process is complete.

With regard to a shape of the rib 70, it is preferable that the rib 70 has a planar shape complementary to one side of the porous layer 30 as the rib 70 supports the porous layer 30 until the porous layer 30 is completely attached to the bone contact surface 101.

Although the rib 70 may be configured to be solid overall in shape, it is preferable to form the rib as a grid shape to include multiple penetration holes 71 in an inner side such that weight of the rib and material, as well as costs, needed for manufacturing can be reduced while the rib is still capable of supporting the porous layer 30. Size of such penetration holes 71 may be determined within a scope in which the porous layer 30 maintains the supporting effect. The connecting layer 50 is absorbed into the bone contact surface 101 and the porous layer 30 through the hot isostatic pressing process but not into the rib 70. Thus, it is preferable to remove the rib 70 from the porous layer 30 when the hot isostatic pressing process is finished. That is, the rib 70 lets the porous layer 30 correctly attach to the bone contact surface 101 through the connecting layer by supporting the porous layer 30 before the hot isostatic pressing process is finished.

Figure 6:
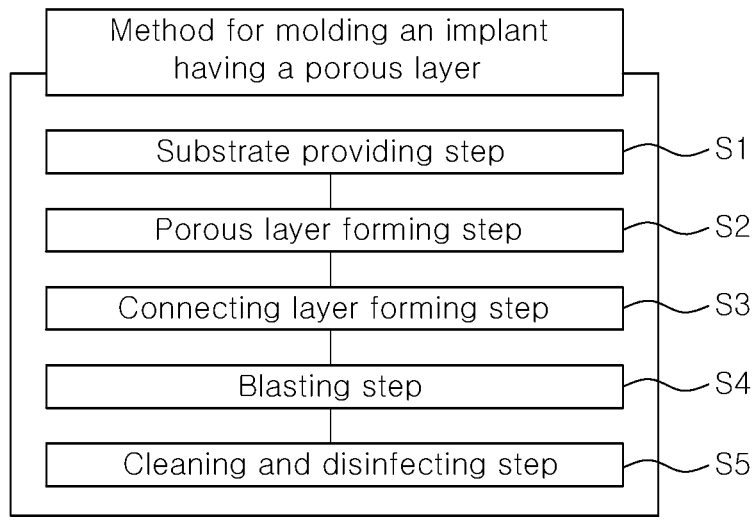
FIG. 6 shows a method for molding an implant having a porous layer according to one embodiment of the present invention.

From now on, description will be made on a method for molding the implant 1 having the porous layer. FIG. 6 shows a method for molding the implant having the porous layer according to one embodiment of the present invention. With reference to FIG. 6, the method for molding the implant 1 having the porous layer according to one embodiment of the present invention comprises: a substrate providing step S1, a porous layer forming step S2, a connecting layer forming step S3, a blasting step S4, and a cleaning and disinfecting step S5.

The substrate providing step S1 is a step in which an orthopedic prosthesis without a porous layer is provided. As described above, the orthopedic prosthesis may preferably be formed by cobalt-chromium-molybdenum (CoCrMo) alloy.

Figure 7:
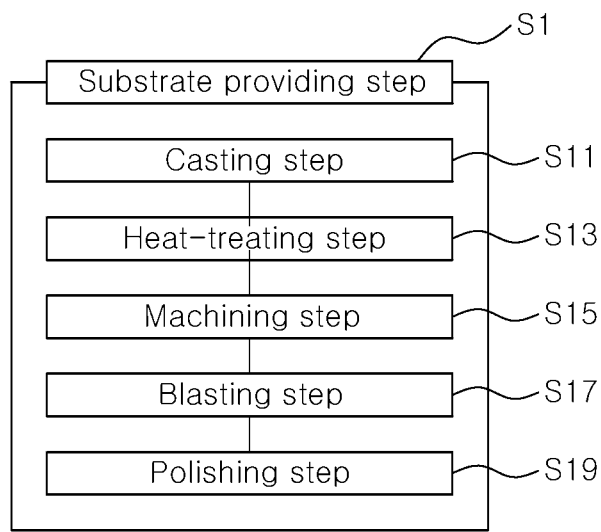
FIG. 7 shows a substrate providing step shown in FIG. 7.

FIG. 7 illustrates the substrate providing step as shown in FIG. 6. The substrate providing step S1 comprises a casting step S11, a heat-treating step S13, a machining step S15, a blasting step S17, and a polishing step S19.

The casting step S11 refers to a step in which an orthopedic prosthesis in a desired shape is manufactured by using cobalt-chromium-molybdenum (CoCrMo) allpy. The heat-treating step S13 refers to a step in which mechanical characteristics of the cast orthopedic prosthesis are changed through processes, such as heating, and cooling and hardening. The machining step S15 corresponds to a step in which the orthopedic prosthesis passing the heat-treating step is trimmed by utilizing machines. The blasting step S17 refers to a step in which impurities, metal oxides and the like are removed from surfaces of the orthopedic prosthesis finished with the machining. The polishing step S19 refers to a step in which the rough surfaces of the orthopedic prosthesis passing through the blasting step are polished by using an abrasive.

The porous layer forming step S2 is a step in which the porous layer 30 being a structure stimulating natural bone growth by forming a void inside is produced. Materials for the porous layer 30 are not limited to a particular material but may preferably be titanium (Ti).

Figure 8:
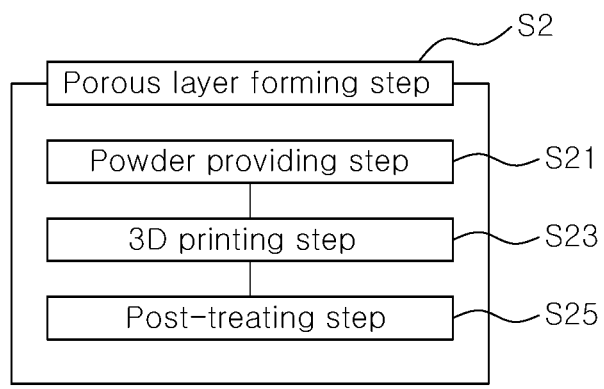
FIG. 8 shows a porous layer forming step shown in FIG. 6.

FIG. 8 shows the porous layer forming step shown in FIG. 6. The porous layer forming step S2 comprises: a powder providing step S21, a 3D printing step S23, and a post-treating step S25.

The powder providing step S21 is a step in which powder is supplied, used in the 3D printing step S23 described later. Types of powder are not limited to a particular type but may preferably be titanium (Ti) powder or alloy powder based on titanium (Ti).

The 3D printing step S23 refers to a step in which a three-dimensional structure of the porous layer 30 is formed by using a DED (Directed Energy Deposition) method in which powder is supplied in real-time, melted immediately after supply by using a high output laser and stacked, or a PBF (Powder Bed Fusion) method in which a powder layer is spread in a powder bed having a certain area in a powder supply device and piled up by fusing layer by layer after a laser or an electron beam is selectively irradiated.

The post-treating step S25 refers to all post-treatment processes which aid in joining and using the orthopedic prosthesis, such as cleaning the porous layer 30 produced through the 3D printing step S23.

Figure 9:
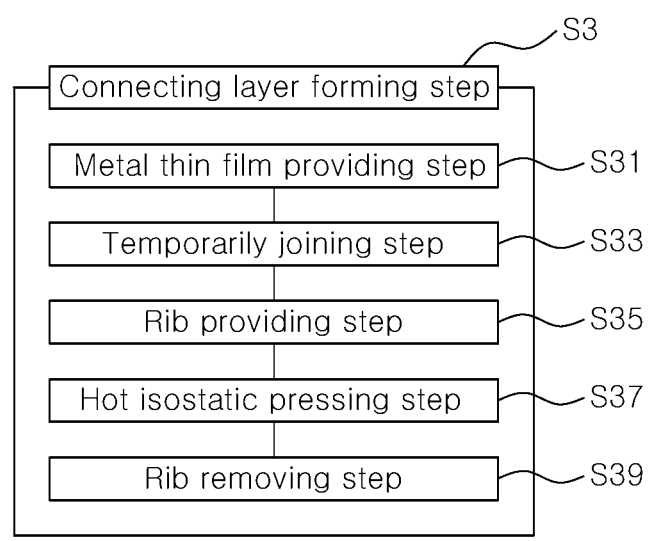
FIG. 9 shows a connecting layer forming step shown in FIG. 6.

FIG. 9 illustrates a connecting layer forming step shown in FIG. 6. Descriptions will be made in reference with FIG. 9.

The connecting layer forming step S3 is a step in which a connecting layer 50 is formed, disposed between the bone contact surface 101 and the porous layer 30 to prompt bonding of dissimilar metals, and the connecting layer 50 is characterized in that the connecting layer 50 is formed by dissolving a metal thin film. That is, when the metal thin film is placed in a lower side of the bone contact surface 101, the porous layer 30 is placed below the metal thin film and then heat and pressure are applied, the connecting layer (50) is formed to prompt joining of the bone contact surface 101 with the porous layer 30.

The material of the metal thin film is not limited to a specific material but may preferably be a molybdenum component, which is one of the components in the substrate 10 having the bone contact surface 101 of cobalt-chromium-molybdenum alloy (CoCrMo). In this case, the metal thin film may be formed as a monolayer (mono, 0.01~0.3 μm) or as polylayers (poyl, 0.3~10 μm).

As shown in FIG. 9, such connecting layer forming step S3 comprises: a metal thin film providing step S31, a temporarily joining step S33, a rib providing step S35, a hot isostatic pressing step S37, and a rib removing step S39.

The metal thin film providing step S31 is a step in which the metal thin film which forms the connecting layer 50 is provided. The metal thin film may preferably be a molybdenum component which is one of the components in the substrate 10 having the bone contact surface 101 of cobalt-chromium-molybdenum (CoCrMo) alloy. The metal thin film may be formed as a monolayer (mono, 0.01~0.3 μm) or polylayer (poyl, 0.3~10 μm). The connecting layer 50 is formed by the dissolved metal thin film.

The temporarily joining step S33 refers to a step in which the metal thin film is temporarily bonded between the bone contact surface 101 and the porous layer 30 through the temporary fixing means. Before the metal thin film forms the connecting layer 50 through the hot isostatic pressing process and completely joins the bone contact surface 101 and the porous layer 30, the bone contact surface 101 and the porous layer 30 are as if the bone contact surface 101 and the porous layer 30 are in a detached state. Accordingly, the temporarily joining step S33 is a process of temporarily fixing the bone contact surface 101, the metal thin film, and the porous layer 30 stably in predetermined, exact positions before the connecting layer 50 completely joins the bone contact surface 101 and the porous layer 30 through the hot isostatic pressing process. The temporarily fixing means is not limited to a particular object but my preferably be an adhesive.

The rib providing step S35 refers to a step in which the rib 70 detachably coupled to the porous layer and supporting the porous layer 30 is provided. The rib 70 is coupled to one side of the porous layer 30 to support the porous layer 30 before the bone contact surface 101 and the porous layer 30 are completely joined such that twisting of the porous layer 30 is prevented. Coupling of the rib 70 and the porous layer 30 may be achieved by using various ways but preferably by mechanical hooking, such as pressing or tongs.

The hot isostatic pressing step S37 refers to a step in which the bone contact surface and the porous layer are joined by applying heat and pressure. That is, the hot isostatic pressing step S37 refers to a step in which, when the connecting layer 50 is disposed between the bone contact surface 101 and the porous layer 30 and dissolved by applied heat and pressure, the connecting layer 50 is fused with the bone contact surface 101 including at least one constitute component identical to that of the connecting layer 50 and simultaneously penetrates into the porous layer to join the bone contact surface 101 and the porous layer 30. Preferably, temperature may range from 900° C. to 1250° C. and pressure may range from 100 MPa to 500 MPa in the hot isostatic pressing step S37. Likewise, the bone contact surface 101 and the porous layer 30 are firmly secured to each other through heating and pressurizing processes and mechanical properties improve at the same time.

In the rib removing step S39, the rib 70 is removed after the hot isostatic pressing step S37. Since joining the rib 70 to the porous layer 30 may preferably be carried out by mechanical hooking, such as tongs, the rib removing step S39 refers to a step where the rib 70 coupled to support the porous layer 30 is removed from the porous layer 30 by removing such tongs.

The blasting step S4 refers to a step in which impurities, metal oxides and the like are removed from the surfaces of the implant 1 having the porous layer after the connecting layer forming step S3. In the blasting step S4, ice-blasting or deburring may be employed.

The cleaning and disinfecting step S5 refers to a step in which the surfaces of the implant 1 forming the porous layer 30 through the connecting layer 50 are cleaned and disinfected. With regard to methods of cleaning and disinfecting, the methods are not limited to particular methods, and various methods which are already known or will be known may be included.

Figure 10:
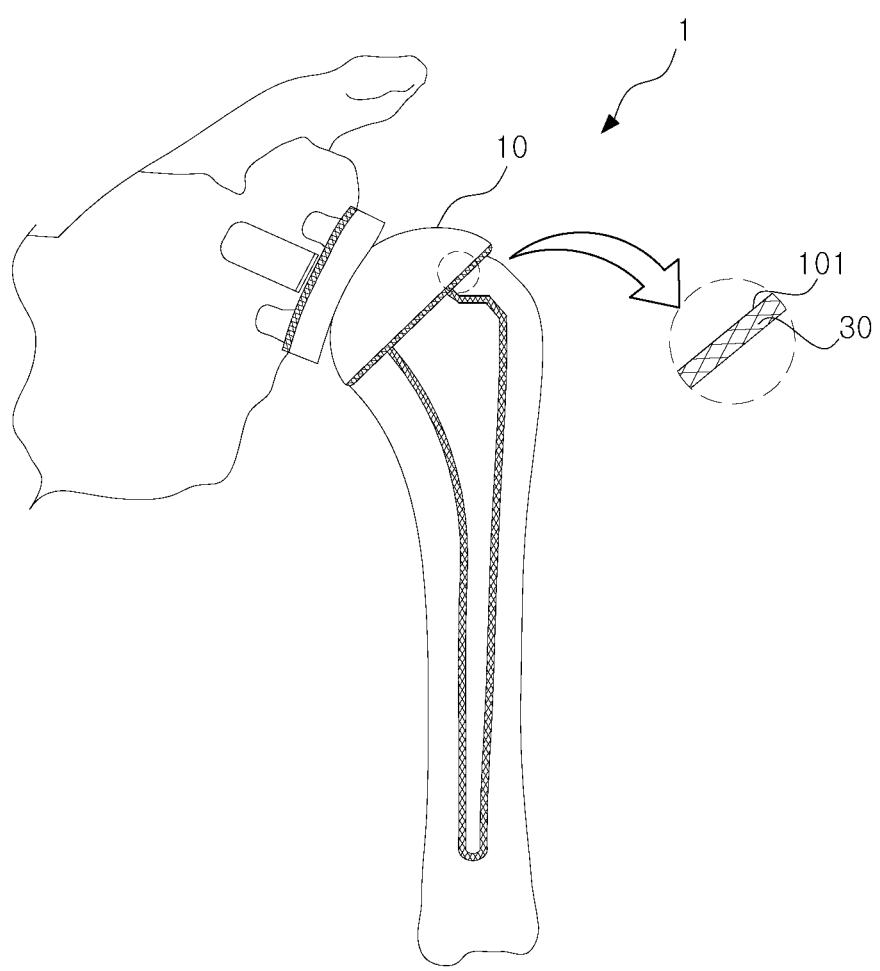
FIG. 10 shows a state of use of a shoulder joint implant having a porous layer according to the present invention.
Figure 11:
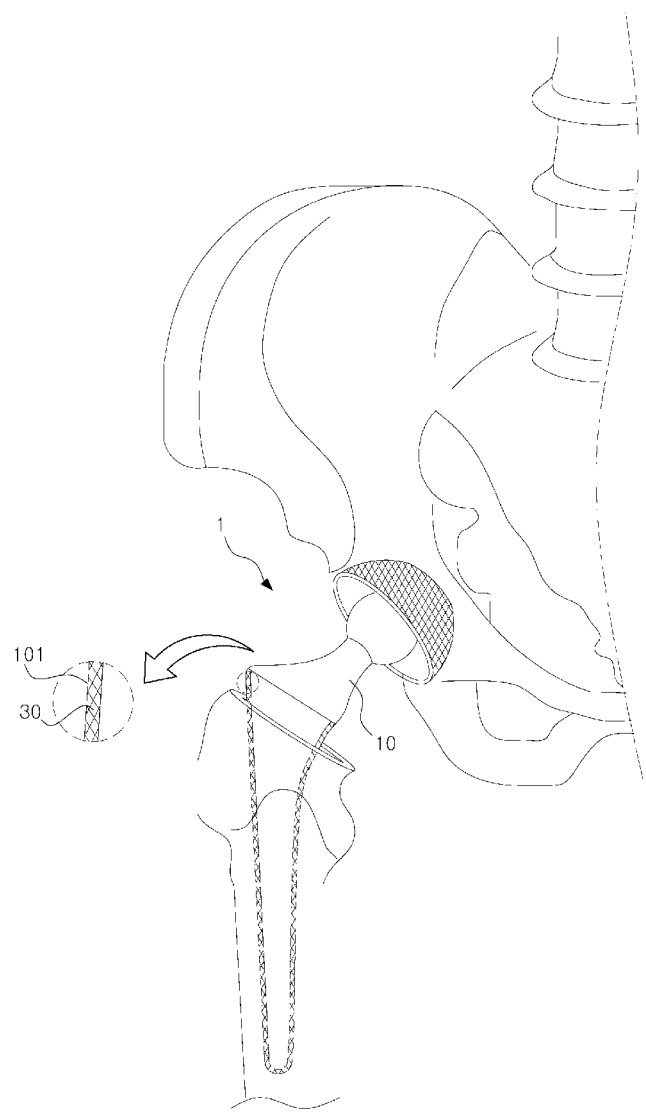
FIG. 11 shows a state of use of a hip joint implant having a porous layer according to the present invention.
Figure 12:
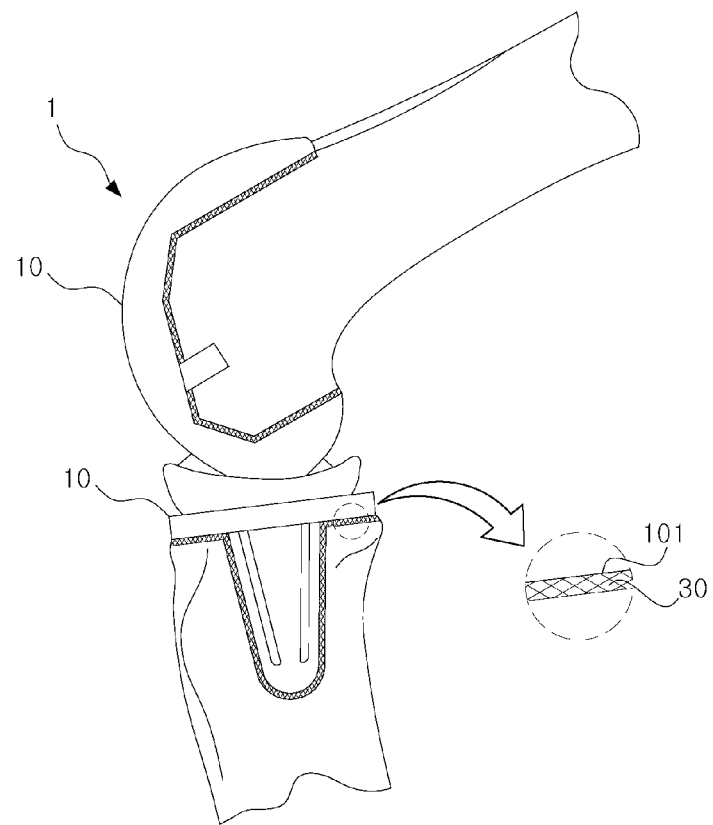
FIG. 12 shows a state of use of a knee joint implant having a porous layer according to the present invention.
Figure 13:
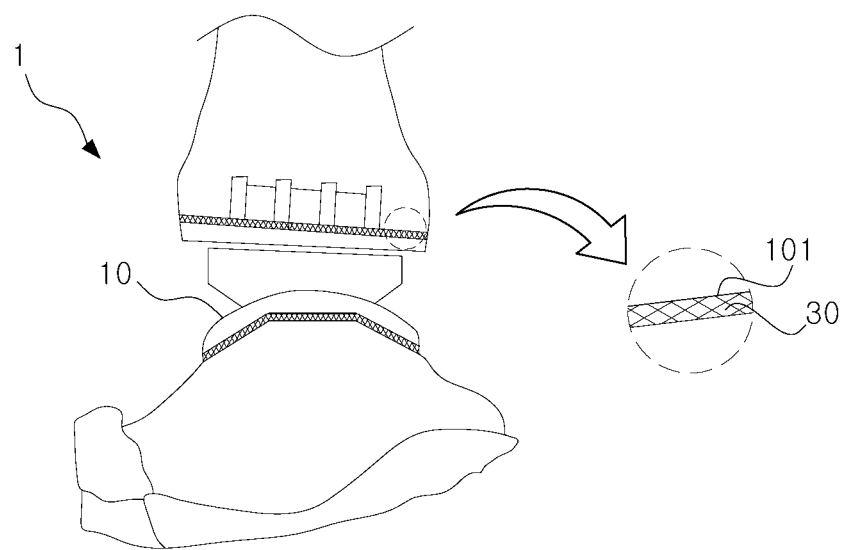
FIG. 13 shows a state of use of an ankle joint implant having a porous layer according to the present invention.

FIGS. 10 through 13 show states of use of the implant having a porous layer. FIG. 10 shows a state of use of the implant for a shoulder joint, having a porous layer, FIG. 11 shows a state of use of the implant for a hip joint, having a porous layer, FIG. 12 shows a state of use of the implant for a knee joint, having a porous layer, and FIG. 13 shows a state of use of the a implant for an ankle joint, having a porous layer.

Referring to FIGS. 10 to 13, in the implant 1 having the porous layer, the porous layer 30 having a shape complementary to the shape of the bone contact surface 101 is attached to a part of the bone contact surface 101 in the substrate 10 directly touching a bone of a patient.

In this case, since the substrate 10 and the porous layer 30 may be formed by different materials, the connecting layer 50 is formed between the bone contact surface 101 of the substrate 10 and the porous layer 30 to facilitate joining of two different materials such that the connecting layer 50 prompts easy joining of the base contact surface 101.

To this end, the metal thin film forming the connecting layer 50 is configured to include one of the constituent components in the bone contact surface 101. Also, the metal thin film naturally melts in the bone contact surface 101 and the porous layer 30 when subjected to heat and pressure through the hot isostatic pressing process and attaches the porous layer 30 to the bone contact surface 101. During this process, the porous layer 30 is supported by the rib 70 for proper joining of the porous layer 30 to prevent twisting.

The implant 1 having the porous layer, manufactured through the series of processes described above, is implanted into a bone of a patient. The bone contact surface 101 in contact with the bone in the implant 1 is provided with the porous layer 30, which can stimulate natural bone growth of the patient. Accordingly, problems, such as an osteolysis phenomenon, disintegration of the prosthesis, and infection, which may occur in an implant joining part after an artificial joint surgery, can be prevented.

The foregoing detailed description illustrates the present invention. Additionally, the disclosure shows and describes the preferred embodiments of the invention, and the present invention can be used in various other combinations, modifications, and environments. In other words, the present invention is capable of changes or modifications within the scope of the inventive concept as expressed herein, commensurate with the above teachings, and/or the skill or knowledge of the relevant art. The embodiments described hereinabove are further intended to explain best modes known of practicing the invention and the various modifications required by specified applications or uses of the present invention can be obtained. Accordingly, the description is not intended to limit the present invention to the form disclosed herein. Also, it is intended that the appended claims be construed to include alternative embodiments.

REFERENCE NUMERALS

10: substrate
30: porous layer
50: connecting layer
70: rib
S1: substrate providing step
S2: porous layer forming step
S3: connecting layer forming step
S4: blasting step
S5: cleaning and disinfecting step

The invention claimed is:

1. An implant having a porous layer, comprising:
a substrate having a lower surface configured to face a bone of a patient during use, the lower surface comprising a first metal;
a porous layer having a void inside, the porous layer comprising a second metal that is dissimilar from the first metal; and
a connecting layer disposed between the lower surface and the porous layer, the connecting layer attaching the lower surface to the porous layer,
wherein the connecting layer comprises a metal thin film, the connecting layer being at least partially melted into the void of the porous layer and being fused with the lower surface of the substrate via at least partial melting of the connecting layer, so that the connecting layer integrates with the porous layer and the lower surface of the substrate to firmly attach the porous layer to the lower surface of the substrate, and
wherein the connecting layer includes at least one constituent component identical to one of constituent components in the lower surface so that the connecting layer and the lower surface are integrally fused by metal bonding.

2. The implant of claim 1, wherein the connecting layer is formed by temporarily joining the metal thin film between the lower surface and the porous layer through a temporary fixing means.

3. The implant of claim 2, further comprising a rib detachably coupled to the porous layer.

4. The implant of claim 1, wherein the implant is any one of a shoulder joint, a hip joint, a knee joint, and an ankle joint.

5. The implant of claim 4, wherein the lower surface is formed by at least one of titanium, titanium alloy, cobalt-chromium, magnesium, and cobalt-chromium-molybdenum alloy.

6. An implant having a porous layer, comprising:
a substrate having a lower surface configured to face a bone of a patient during use;
a porous layer having a void inside; and
a connecting layer disposed between the lower surface and the porous layer, the connecting layer attaching the lower surface to the porous layer,
wherein the connecting layer comprises a metal thin film that is secured to the porous layer and is fused with the lower surface of the substrate via at least partial melting of the connecting layer, and
wherein the connecting layer includes at least one constituent component identical to one of constituent components in the lower surface of the substrate so that the connecting layer and the lower surface are integrally fused.

7. The implant of claim 1, wherein the porous layer comprises a second metal that is dissimilar from the first metal of the lower surface so that the porous layer and the lower surface do not share a common constituent component.

8. An implant having a porous layer, comprising:
a substrate having a lower surface configured to face a bone of a patient during use, the lower surface comprising a first metal;
a porous layer having a void inside, the porous layer comprising a second metal that is dissimilar from the first metal; and
a connecting layer disposed between the lower surface and the porous layer, the connecting layer attaching the lower surface to the porous layer,
wherein the connecting layer comprises a metal thin film, the connecting layer being at least partially melted into the void of the porous layer and being fused with the lower surface of the substrate via at least partial melting of the connecting layer, so that the connecting layer integrates with the porous layer and the lower surface of the substrate to firmly attach the porous layer to the lower surface of the substrate,
wherein the connecting layer includes at least one constituent component identical to one of constituent components in the lower surface, and
wherein the porous layer comprises a second metal that is dissimilar from the first metal of the lower surface so that the porous layer and the lower surface do not share a common constituent component.

9. The implant of claim 8, wherein the connecting layer comprises a third metal including the at least one constituent component identical to one of constituent components in the lower surface, the third metal not being identical to the first metal of the lower surface.

* * * * *